United States Patent [19]

Kraemer et al.

[11] Patent Number: 4,829,101

[45] Date of Patent: May 9, 1989

[54] POLYMER PARTICLES AND LATICES THEREOF FOR THE IMMOBILIZATION OF BIOLOGICALLY ACTIVE SUBSTANCES

[75] Inventors: Dieter Kraemer, Mainz; Werner Siol, Pfungstadt; Gerhard Markert; Norbert Suetterlin, both of Ober-Ramstadt; Cornelia Feil, Erzhausen, all of Fed. Rep. of Germany

[73] Assignee: Röhm GmbH, Darmstadt, Fed. Rep. of Germany

[21] Appl. No.: 75,416

[22] Filed: Jul. 20, 1987

Related U.S. Application Data

[60] Division of Ser. No. 930,023, Nov. 7, 1986, Pat. No. 4,710,525, which is a continuation of Ser. No. 827,222, Feb. 5, 1986, abandoned, which is a continuation of Ser. No. 369,099, Apr. 16, 1985, abandoned.

[30] Foreign Application Priority Data

Apr. 29, 1981 [DE] Fed. Rep. of Germany ....... 3116995

[51] Int. Cl.$^4$ ............................................... C08L 83/00
[52] U.S. Cl. .................................... 523/201; 525/286; 525/902
[58] Field of Search .................. 523/201; 525/286, 902

[56] References Cited

U.S. PATENT DOCUMENTS

| | | | |
|---|---|---|---|
| 3,660,525 | 5/1972 | Kawahara | 525/902 |
| 3,661,994 | 5/1972 | Hwa et al. | 260/879 |
| 3,787,522 | 1/1974 | Dickie et al. | 525/902 |
| 3,856,883 | 12/1974 | Dickie et al. | 525/902 |
| 4,107,120 | 8/1978 | Plamondon et al. | 523/201 |
| 4,138,383 | 2/1979 | Rembaum et al. | 260/29.7 H |
| 4,140,662 | 2/1979 | Reckel et al. | 260/8 |
| 4,181,636 | 1/1980 | Fischer | 260/8 |
| 4,210,723 | 7/1980 | Dorman et al. | 435/180 |
| 4,217,260 | 8/1980 | Daniel et al. | 523/201 |
| 4,226,747 | 10/1980 | Boncari | 523/201 |
| 4,331,784 | 5/1982 | Ishibashi | 525/902 |

FOREIGN PATENT DOCUMENTS

| | | |
|---|---|---|
| 2812845 | 9/1978 | Fed. Rep. of Germany . |
| 2833510 | 2/1979 | Fed. Rep. of Germany . |
| 2005275 | 4/1979 | United Kingdom . |
| 2004892 | 4/1979 | United Kingdom . |
| 2041940 | 9/1980 | United Kingdom . |

OTHER PUBLICATIONS

"Enzyme Engineering", Biotechnology and Bioengineering Symposium, No. 3, Interscience, New York, (1972), pp. 160, 161 and 179.

"Fermentation Advances", ed. by D. Perlman, Academic Press, New York (1969), pp. 391-393.

"The Peptides", Schroeder et al., vol. I, Academic Press, New York and London, 1965, pp. 97-108.

*Primary Examiner*—Joseph L. Schofer
*Assistant Examiner*—J. M. Reddick
*Attorney, Agent, or Firm*—Curtis, Morris & Safford

[57] ABSTRACT

Polymer particles dispersible to form a latex and latices of such polymer particles, said particles being adaptable to the fixing or bonding thereto of a biologically active substance and having a core-shell construction wherein the polymer material of the core determines the stability of the form of the latex particles and their redispersibility, and the material of the shell (1) is so hydrophilic that it would be completely or largely water soluble if it were not anchored to the core material and/or crosslinked, (2) contains functional groups which are suitable for the covalent fixation or bonding of biological active substances, and (3) in an anhydrous condition has a $T_{\lambda max}$ from 20°-250° C., depending on its composition, and methods for bonding a biologically active substance to such particles, for example to prepare a diagnostic reagent.

12 Claims, No Drawings

POLYMER PARTICLES AND LATICES THEREOF FOR THE IMMOBILIZATION OF BIOLOGICALLY ACTIVE SUBSTANCES

This application is a divisional application of Ser. No. 930,023 filed Nov. 7, 1986, now U.S. Pat. No. 4,710,525 granted Dec. 1, 1987; which in turn is a continuation application of Ser. No. 827,222 filed Feb. 5, 1986 and now abandoned; which in turn is a continuation application of Ser. No. 369,099 filed Apr. 16, 1982 and now abandoned.

The present invention relates to certain polymer particles dispersible to form a latex, to latices of such polymer particles, and to methods for immobilizing (i.e. bonding or fixing) a biologically active substance on such particles, which have a core-shell construction and comprise groups in the shell region suitable for the covalent fixation to the particle of a biologically active substance.

The problem of fixing biologically active substances onto a carrier is posed in manifold aspects in the area of technology, for example in biochemistry and biotechnology, and in medicine, particularly in medical diagnostics, inter alia. As a rule, the "biologically active substances" to be fixed are compounds or functional units which are capable of a mutual exchange with biological systems, or are these biological systems themselves.

The fixation of catalysts, especially of enzymes but also of substrates, such as are of significance for affinity chromatography for example, is of particular interest in technology. In order to explain the existing technical problems, the immobilization of such "biologically active substances" as can be diagnostically evaluated will be described more in detail below.

In such reactions capable of diagnostic evaluation, the matter is one of detecting the mutual interaction of substances which are present in an organism, or are produced by an organism, and which are symptomatic of the condition which is to be detected diagnostically, with such substances as interact as specifically as possible with these "symptomatic" substances. An extraordinary high degree of specificity is exhibited by immune reactions. As is known, immune reactions occur between antigens and antibodies: one of the two reaction partners must be known so that the other can be determined qualitatively or quantitatively in a body fluid or can be localized in cells and tissues.

There are various analytic methods for the determination of antigen-antibody reactions, for example radioimmunoassay, enzymeimmunoassay, immunofluorescence, immunodiffusion, and, particularly, immunoagglutination.

Immunoagglutination makes possible the detection of even low concentrations of immunologically active materials, making use of a particulate carrier as an indicator, the clumping of which makes evident, visually or photometrically, the occurrence of of an immune reaction.

According to the kind of carrier employed, distinctions are made between erythrocyte agglutination (or its inhibition) and latex agglutination (or its inhibition).

Relatively considerable attention has been given to latex agglutination.

The proposed latices can belong to different polymer types. Frequent use is made of latices comprising styrene or styrene-containing copolymers (carboxylated polystyrene, carboxylated polystyrene-butadiene copolymers, styrene-divinylbenzene, styrene-acrylamide, acrylonitrile-butadiene-styrene, styrene-methacrylate), or comprising anionic phenolic resins, diazotized aminocellulose in the form of fine particles, etc.

Latices comprising (meth)acrylates have also been proposed. According to U.S. Pat. No. 4,138,383, polymers of acrylate monomers containing —OH, —NH₂, or —COOH groups have been prepared in the presence of crosslinking agents in the form of suspensions of round microspheres having a uniform diameter equal to or less than 2000 Angstrom units. Immunoglobulins G (IgG) have been bound to these latex microspheres using carbodiimide or glutaraldehyde as a condensation agent. Experiments for modifying the construction of the latex particles have also been undertaken.

Thus, German Offenlegungsschrift 28 40 768 proposes carriers to which a water soluble polyhydroxy compound is covalently bound. The last-mentioned application proposes a particle size in the region from 0.01 to about 0.9 micron and a density near that of water. The latex materials should be inert with respect to immunological diagnostic tests and should have active groups which make possible a covalent bonding with a polyhydroxy compound. To the extent that the described conditions are fulfilled, any latex polymer is said to be suitable.

In Belgian Pat. No. 874,588, latex particles having a shell structure and a diameter from 0.15–1.5 microns are recommended. In this case, the core is to be formed by the polymerization or copolymerization of "hard" monomers and the exterior covering is to be prepared by the copolymerization of one or more "hard" monomers with an ethylenically unsaturated compound having free epoxy groups.

For example, the free radical polymerization of styrene and glycidyl methacrylate in the presence of a polystyrene latex is described. The latex so formed can be loaded with, for example, human chorionic gonadotropin.

However, to date, a technical realization of the latex concept in immune diagnosis has not gone further than a certain few steps.

Among the limiting factors are, for example, a bonding of the biologically active substances (e.g. of an antibody). Until now, the biologically active substances have been predominantly bound onto the latex adsorptively. As a result of this, almost inescapable problems arise because of the diffusion of the only loosely bound biomacromolecule.

In certain cases—as already mentioned—use is made of a covalent bonding of the biologically active substance. In general, this involves bonding functions or groups which must be introduced in several method steps, mostly the introduction of —COOH— or —NH₂ groups by reactions analogous to polymerization as well as subsequent coupling with a protein with the aid of (soluble) carbodiimides or of glutardialdehyde. As an example, the multi-stage covalent immobilization described in German Offenlegungsschrift 28 12 845 should be mentioned.

Latices of particles having a core-shell construction are known from German Offenlegungsschrift No. 28 33 510, in which latices the polymer particle core is a vinyl- and/or diene-polymer having carboxylic acid and/or sulfonic acid groups, and the shell is a vinyl polymer having terminal amine-substituted thiophenol ether groups. Activation of the latex particles can take place, for example, by means of diazotization.

Instead of a covalent fixation involving a multi-stage process, attempts have also been made to prepare latices of particles having permanent groups capable of reaction, for example oxirane groups. However, these exhibit only a limited storage stability. The subsequent purification steps, which are as complicated as they are indispensable, must be considered as perhaps the most serious disadvantage of the latices used for the fixation of biologically active systems. For the covalent fixation of proteins onto the particles of a latex, for example all auxiliary substances (e.g. the urea which is formed in the case of a carbodiimide coupling) and above all, unbound protein, must be removed in protracted purification steps, for example by ultrafiltration. These time consuming and expensive operations practically exclude any meaningful use of first rate materials, even those not particularly biologically stable.

Thus, the problem existed of providing latices the use of which would not involve the disadvantages described earlier, or would involve them only to a slight degree.

In any event, certain limits arising from physical phenomena are set on the technology of latices. Thus, latex particles are known to represent a metastable system which can only be maintained stable in the presence of surface active agents and only for a limited period of time. Latex particles show instability particularly toward elevated electrolyte concentrations. However, since physiologically relevant processes occur in solutions containing electrolytes (e.g. in 0.9 percent sodium chloride solution), the use of conventional latex particles is very difficult, particularly if it is a matter of detecting the small amounts of substances which are characteristically involved in diagnostic work. Agglutinations can be feigned as soon as there is any drying, for example, and even only concentration leads to a precipitation of the latex particles. Stabilization by the use of a high concentration of emulsifier is not to be recommended because of the denaturing effect of emulsifiers on biological systems. To be sure, a stabilizing effect can be evoked in the latex particles by the inclusion of strongly ionic groups, but at the same time the properties of the latices which are determining for the biospecific mutual effect are disadvantageously influenced.

In this way, a series of demands are made on latices which are proposed to be used for the immobilization of biologically active substances:

the particles of the latices should have reactive groups which make possible a covalent bonding of the biologically relevant molecule under physiological conditions;

the particles of the latices should be capable of being stored as anhydrous solids in order to assure a constancy in the content of reactive groups therein over a long period of time;

the particles of the latices should be fully redispersible so that their drying is not critical to their availability;

and the latices should be capable of centrifugation, a requirement which is fulfilled if the density of the particles therein is sufficiently different from the density of the carrier medium or of the continuous phase. If the density of the particles is greater than that of the surrounding medium, separation of the particles can be effected by sedimentation; if their density is less than that of the surrounding medium, separation can be by flotation.

It has now been found that polymer particles having a core-shell construction are particularly suitable for the covalent immobilization of biologically active substances or structures, particularly from the point of view of a diagnostic use.

According to the invention, the shell of the core-shell polymer particle comprises a material capable of being swollen by water. The shell material shall be hydrophilic to such a high degree, as a result of its composition, that it would be at least partially soluble in water if it were not anchored to the core material and/or if it were not crosslinked. Thus, the shell can also be crosslinked within itself. The solution of the shell of the latex particle in surrounding water is thus hindered by bonding to the particle core, e.g. as a result of grafting and-/or crosslinking.

Further, the shell has the functional groups which are necessary for the covalent fixation of biologically active substances or structures. For example, such functional groups, known per se, are used as will react in aqueous solution with nucleophiles stronger than water and which are not attacked, or are attacked only in small degree, by water in the physiologically meaningful pH-region, i.e. particularly in the region from 6.0 to 9.0, particularly from 6.5 to 8.0.

The choice of the functional groups takes into consideration that the material to be fixed, particularly material of a biological origin, generally contains the (free) amino group as the nucleophilic group, but possibly also phenolic, hydroxy, or thiol groups in addition.

The polymer of said shell comprises (a) from 4.9 to 99.9 percent, by total weight of the polymer material of said shell, of a combination of at least one monomer having a functional group and at least one hydrophilic monomer, but the content of said monomer having a functional group being at least 0.1 percent;

(b) from 0 to 95 percent by weight of at least one non-hydrophilic monomer; and (c) from 0.1 to 20 percent by weight of at least one crosslinking monomer.

The construction of the shell portion of the latex according to the present invention in its reactive form can thus be represented as follows in a highly schematized manner;

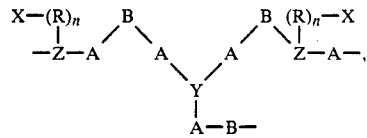

wherein X represents the functional groups to be covalently bonded, preferably those which fulfill the conditions described earlier; R represents a spacer between the functional and the polymerizable groups, with the size and type of the spacer bering comparatively uncritical; Z represents the polymerized form of a polymerizable group Z', present in a polymerizable monomer of the type $Z'-(R)_n-X$, discussed more in detail hereinafter; B represents a hydrophilic component of the shell derived from one or more hydrophilic monomers described more in detail hereinafter; A represents a component imparting hardness or rigidity of form to the shell and is also described more in detail below; and n has the value 0 to 1, respectively defining embodiments in which a spacer, R, is absent or present between groups Z and X. In a number of examples, the group R can be entirely absent, i.e. n can have the value 0.

As a rule, X signifies a group which can react with one of the nucleophiles in question, i.e. is an activated group. Preferably, it signifies a sulfonic acid halide group, a thioisocyanate group, an activated ester, or a thiocarbonyldioxy-, carbonylimidoyldioxy-, haloethoxy-, haloacetoxy-, oxirane-, aziridine-, formyl-, keto-, acryloyl-, or anhydride-group.

As sulfonic acid halides, the chloride and bromide can be used. The fluoro, chloro, and bromo compounds can be used as haloacetoxy compounds. As ester components, the activated esters of hydroxylamine compounds (such as those of N-hydroxysuccinimide or of N-hydroxyphthalimide), of phenols activated with electron-attracting groups (such as halophenols like trichlorophenol, or of nitrophenols), or of heterocyclic lactams such as pyridone can be used.

Oxirane, keto, formyl, sulfonic acid chloride, thioisocyanate, activated carboxylic acid ester, and carboxylic acid anhydride groups are particularly preferred. Among the monomers of the type $Z'—(R)_n—X$, $Z'$ represents a (free radically) polymerizable unit and n is 0 or 1.

Such free radically polymerizable units are, for example, vinyl groups wherein $Z'$ for example represents

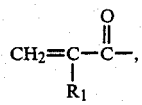

wherein $R_1$ is hydrogen or methyl or is $—CH_2—COOR_2$, $CH_2—CONHR_2$, or is $—CH_2—CON(R_2)_2$, wherein $R_2$ is alkyl having 1 to 4 carbon atoms.

Further, $Z'$ can be derived from maleic acid

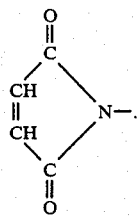

As groups which are both polymerizable and capable of reaction, maleic acid anhydride and itaconic acid anhydride, as well as acrolein, methacrolein, methylvinylketone, and activated esters will serve. Derivatives of (meth)acrylic acid and of maleiimide, as well as maleic acid anhydride and itaconic acid anhydride, are particularly preferred.

The following examples are given for elucidation of the formula $Z'—R—X$:

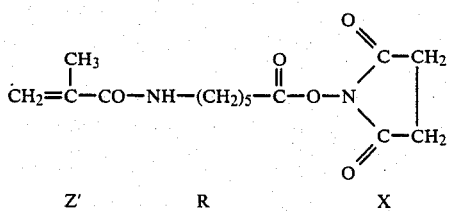

-continued
(polymerizable activated ester with a spacer)

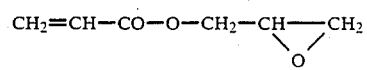

Z'     R     X (Glycidyl acrylate)

$CH_2=CCH_3—CO—O—CH_2—CH_2—O—\underset{\underset{O}{\|}}{C}—CH_2—Cl$

Z'     R     X

[2-(chloroacetoxy)-ethyl methacrylate]

$CH_2=CCH_3—CO—O—C_6H_2Cl_3$

Z'     X (2,4,5-trichlorophenyl methacrylate) R = 0
$CH_2=C(CH_3)—COO—CH_2—CH_2—Br$
(2-bromoethyl methacrylate)

$CH_2=C(CH_3)COOCH_2CHOHCH_2O(CH_2)_4OCH_2CH—CH_2$

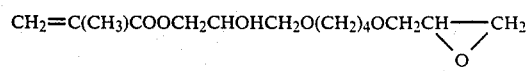

(condensation product of methacrylic acid and 1,4-butanediol diglycidyl ether)
$CH_2=CH—COO—CH_2—CH_2—O—CSNH—(CH_2)_6—N=C=S$
(condensation product of acrylic acid-2-hydroxyethyl ester with 1,6-hexanediisothiocyanate)
$CH_2=CH—O—CO—CH_2—Cl$
(chloro acetic acid vinyl ester)

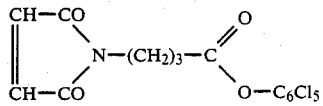

(4-maleimido-butyric acid-pentachlorophenyl ester)
$CH_2=C(CH_3)—COO—C_6H_4—SO_2—CH_3$
[(4-methylsulfonylphenyl)-methacrylate]
$CH_2=CH—COO—CH_2—C≡C—H$
(propargyl acrylate)

As to the remaining units contributing to the structure of the shell (A and B in the schematic representation), these are by definition such as impart the required properties, namely hydrophilicity and hardness, to the shell. A $T_{\lambda max}$ between 20° and 250° C., particularly between 50° C. and 200° C. (as determined by DIN 53445) can serve as an indication of the desired hardness in an anhydrous condition.

On the other hand, the monomers involved in the construction of the shell should themselves suitably contain no strongly nucleophilic groups (such as $—NH_2$, $—SH$). Further, the shell should preferably not contain any aromatic groups. Further, the components of the shell must in some way be crosslinked. Y serves as a symbol for this crosslinking or for the bonding with the core.

Referring further to the schematic representation, the component primarily responsible for the hydrophilicity of the shell portion is designated as B. Further components, the choice of which must be primarily coordinated with the resulting hardness of the overall polymer, are designated as A.

The conditions described for the shell construction of the latex to be used according to the present invention are met, for example, by copolymers of the methacrylate and/or acrylate type, wherein the qualitative and quantitative amount of component B is so measured that the criteria given earlier herein for the shell of the polymer latex are met.

For example, as the hydrophilic component B, substituted methacrylamides and acrylamides of the general formula

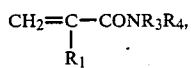

$$CH_2=C-CONR_3R_4,$$
$$\quad\quad|$$
$$\quad R_1$$

can be used, wherein $R_1$ is hydrogen or methyl and $R_3$ and $R_4$, independently of each other, can be hydrogen and/or alkyl having 1 to 4 carbon atoms, that is unsubstituted amides as well as amides formed with primary and secondary amines. (Meth)acrylamide, N-methyl- or N-isopropyl- or N-butyl-(meth)acrylamide, and N,N-dimethyl-(meth)acrylamide should be especially mentioned, as well as (meth)acrylic acid morpholide (a particular case in which $R_3$ and $R_4$, together with the nitrogen atom to which they are attached, form a ring), and N-vinyl-pyrrolidone-2.

Other hydrophilic components B include acrylate or methacrylate monomers containing hydroxy groups, particularly esters or amides of acrylic acid or of methacrylic acid containing hydroxy groups, as well as alkoxyalkyl esters and/or alkoxyalkyl amides of acrylic acid and of methacrylic acid, e.g. representatives of the general formula

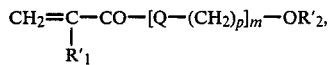

$$CH_2=C-CO-[Q-(CH_2)_p]_m-OR'_2,$$
$$\quad\quad|$$
$$\quad R'_1$$

wherein $R'_1$ is hydrogen or methyl, $R'_2$ is hydrogen or alkyl having 1 to 4 carbon atoms, Q is oxygen or —$N(R_3')$—, wherein $R_3'$ is hydrogen or alkyl having 1 to 4 carbon atoms, p is an integer from 1 to 3, preferably 2, and m is an integer from 1 to 25. However, if Q is oxygen, then p is not equal to 1. Hydroxyethyl acrylate, hydroxyethyl methacrylate, 2-hydroxyethyl (meth)acrylamide, 2-hydroxypropyl(meth)acrylamide, and monoesters of (meth)acrylic acid with glycerine and other polyols are especially mentioned.

Further, 2-(methylsulfinyl)ethyl- acrylate and -methacrylate, as well as N-[2(methylsulfinyl)ethyl]acrylamide and -methacrylamide, are included within monomer type B. Polymerizable acids such as (meth)acrylic acid, itaconic acid, or maleic acid can also be incorporated as hydrophilic groups in the shell of the latex, as can polymerizable tertiary amines like 2-N,N-dimethylaminoethyl-(meth)acrylamide or -(meth)acrylic acidc esters or 3-N,N-dimethylaminopropyl-(meth)acrylamide or -(meth)acrylic acid esters. To avoid imparting a net electrical charge to the latex particles, these acid or basic groups should always be simultaneously present in a particle (e.g. methacrylic acid and 2-N,N-dimethylaminoethyl methacrylate), so that the particles are substantially electrically neutral.

As monomers of type A, those monomers are employed which are insoluble in water or have at most limited water solubility, whereby the qualitative and quantitative amount is so measured that the hardness criterion for the resulting polymer mentioned earlier is satisfied.

Typical of these monomers are:

(a) esters of acrylic acid and/or of methacrylic acid with alcohols having from 1 to 20 carbon atoms, particularly the methyl, ethyl, propyl, and butyl esters of methacrylic acid, as well as the methyl, ethyl, propyl, butyl, and 2-ethylhexyl esters of acrylic acid, and (b) polymerizable monomers of the vinyl acetate type, particularly vinyl acetate, vinyl propionate, vinyl butyrate, and vinyl isobutyrate.

It is understood that the so-called "soft" monomers of type A can only be present in subordinate amounts, generally less than 50 percent by weight of the polymer of the shell.

The hardness or other relevant properties of the polymer films formed from specific monomers is known, as is also the contribution of such monomers to the properties of copolymers in which they are present. [See U.S. Pat. No. 2,795,564; Rauch-Puntigam et al., "Acryl- und Methacryl-verbindungen" ("Acrylic and Methacrylic Compounds"), Springer-Verlag, Berlin, 1967, pages 303–304; T. G. Fox, Bull. Am. Phys. Soc. 1, 123 (1956)].

The amount of the crosslinking agent Y is so measured that a washing away of the latex shell is no longer possible: as a rule at least 0.1 percent by weight of the material is necessary for this purpose. Larger amounts of crosslinking agent are in no way interfering, so that as a rule amounts from 0.1 to 20 percent, particularly from 1 to 10 percent, by weight are used.

From a chemical viewpoint, Y can be any multi-functional acrylate or methacrylate, e.g. glycol dimethacrylate, butanediol diacrylate, triethyleneglycol dimethacrylate, tetraethyleneglycol diacrylate, and pentaerythritol tetraacrylate, inter alia. Not all functional OH groups of the polyol which is used as a basis for the crosslinking agent need be esterified with polymerizable acids (e.g. pentaerythritol dimethacrylate has two free OH groups), so that these crosslinking agents also can exhibit a thoroughly hydrophilic character. A further example for a hydrophilic crosslinking agent, Y, is N,N-methylene-bis-(methacrylamide).

In addition, naturally, such monomers which contain easily graftable units in addition to an easily polymerizable group, e.g. allyl methacrylate, are also useable as crosslinking agents.

The core of the core-shell particles according to the present invention is not fundamentally critical, as long as the condition is met that the resulting latex particles have a stable form, i.e. exhibit sufficient rigidity. From the point of view of technology, the redispersibility of the core-shell latex system should be guaranteed. The polymer material of the core can, for example, meet these requirements as well if it is a material which is soft per se but is a strongly crosslinked polymer as if it is per se a hard polymer (whether crosslinked or not crosslinked). It is in the nature of the core-shell construction that disturbing interactions which could be caused by the core material are less to be feared, so that also from this aspect a relatively free choice of materials exists. Thus, the core can be the carrier of a property suitable for physical separation or identification, e.g. the carrier of a marking which is detectable in a physical manner. For example, one can think of the use of dyes or fluorescent dyes, or of radioactive marking of the core, inter alia. Further, the core can make a physical separation possible as a result of a difference between its density and that of the surrounding medium.

Accordingly, it is possible to construct the core material from such monomers or comonomers as are compatible with the requirement for a redispersibility of the latex, e.g. all copolymer compositions from derivatives of methacrylic acid and of acrylic acid as well as various vinyl esters which impart to the copolymer a $T_{\lambda max}$ (according to DIN 53445) of at least 0° C. These "hard" copolymers are, for example compolymers comprising methyl methacrylate, butyl methacrylate, and methyl acrylate, inter alia, and need not be crosslinked. Whereas care must be taken to avoid the presence of aromatic groups in the region of the shell material if the particles are to be used for diagnostic reagents involving antigen-antibody reactions (because of potential hapten properties), monomers of the styrene type can also be employed in the core of the latex, e.g. styrene, vinyl toluene, divinylbenzene, and, therewith, also copolymers of styrene and maleic acid esters or fumaric acid esters.

If the glass transition temperature, $T_{\lambda max}$, of the core polymer is clearly below 0° C., i.e. if the polymer is instrinsically "soft", then the use of at least 1 percent of a crosslinking agent is recommended, e.g. glycol dimethacrylate, divinylbenzene, etc.

In connection with the requirement for a density of the core particles which deviates from the density of the carrier medium or the continuous phase, such monomers which impart an increased density to the latex acquire a particular significance.

In particular, "heavy" monomers offer themselves, especially those having one or more halogen atoms, and particularly chlorinated or brominated monomers. Mentioned as exemplary are vinyl compounds such as vinyl chloride, styrene derivatives such as chlorostyrene or bromostyrene, as well as derivatives of (meth)acrylic acid which carry these heavy groups in a side chain, e.g. 2,4,6-tribromophenoxyethyl methacrylate.

Alternatively, the core can also be constructed of monomers whose density, as a polymer, distinguishes itself less strongly from the density of the carrier medium or of the continuous phase. In such a case, the size of the core is to be increased to such an extent that nevertheless good separability is guaranteed.

The preparation of latices of core-shell particles of the kind of interest to the present invention can take place following techniques known per se (cf. German Auslegeschrift No. 27 22 752). As exemplary of a preferred embodiment, methods for the preparation of a core-shell latex material having coarse particles and of one having fine particles are given further below.

Whether a latex is to comprise coarse or fine particles is suitably determined by the nature of the core material. The preparation of a coarse-particle polymer core can result, for example, from a polymerization which is completely free of emulsifier.

An advantageous embodiment involves dropping the monomer or a monomer mixture over a period of one-half to four hours into water pre-heated to about 50° to about 100° C. which contains a sufficient amount of a water soluble initiator, such as potassium- or ammonium-peroxydisulfate, hydrogen peroxide, or salts of 4,4'-azobis(cyanovalerianic acid). Instead of a thermal polymerization in the region of about 50° C. to 100° C., however, the reaction can also be initiated at lower temperatures with the aid of a redox initiator sytem. Oil soluble initiators, too, for example dibenzoyl peroxide or azo-bis-isobutyronitrile, are suitable as polymerization initiators. In this case, the use of at least small amounts of an emulsifier is advantageous, or may even be necessary. Another way for achieving large latex particles involves a multi-stage process with the aid of a seed latex. In this case, the desired monomer or monomer mixture is polymerized in a second or even subsequent stage onto a seed latex which has been priorly prepared in a desired manner. Procedurally, batch processes, multiple-batch processes, and also, and better, monomer-feed or emulsion-feed processes are suitable. It is essential for these embodiments that the total emulsifier concentration in the stages following the seed latex is kept so low that all of the monomer polymerizes on the seed latex particles and there is no new particle formation. Particularly large polymer cores are obtained if the aforementioned latices having coarse particles and prepared without an emulsifier are employed as the seed latex (cf. European patent publication No. 79101398.0 or German Offenlegungsschrift No. 28 33 601).

Systems having coarse particles are also obtained if a seed latex is prepared in a first stage to contain a polymer of very low molecular weight. These latex particles can be swollen with monomer or a monomer mixture and polymerized to form large latex particles. The additional use of subordinate amounts of a completely water insoluble substance with the monomer or monomer mixture can have the same effect as the low molecular weight polymer (cf. German Offenlegungsschrift No. 27 51 867 or European Pat. No. 0 003 905). Coarse particle cores, for example having a diameter from about 0.5 to more than 2 microns, are advantageous if the density of the core polymer does not deviate significantly from the density of the carrier medium or of the continuous phase.

The preparation of a polymer core comprising fine particles involves, in principle, the synthesis of a latex according to the known criteria for an emulsion polymerization, wherein the desired size of the core latex particles is controlled at the beginning of the polymerization by the emulsifier concentration. As a result of the fact that the composition of the core material is relatively uncritical, it is in principle here possible also to use any desired latex as the core material, to the extent that the particles herein fulfill the aforementioned requirements such as form stability and high density, for example. For the preparation of a fine-particle core material, one stage or multi-stage batch processes, monomer-feed or emulsion-feed processes, or continuous modes of operation are suitable as methods. As initiators, those water soluble or oil soluble starters mentioned in a preceding paragraph for the preparation of a coarse-particle core latex can be used. As there taught, the polymerization can be purely thermal or may occur with the aid of redox system.

In principle, all anionic, cationic, non-ionic, or amphoteric surface active agents, alone or in combination, are suitable as emulsifers. However, anionic and/or non-ionic emulsifers are preferred. A particularly advantageous embodiment for the preparation of fine-particle core latices involves heating a solution of a suitable buffer (about pH 7) containing an emulsifier to the desired polymerization temperature, adding a water soluble initiator in a certain amount, and then adding a monomer emulsion (including a crosslinking agent) dropwise over a period of 0.5 to about 6 hours. Fine particle cores, for example from about 0.1 to 0.5 micron in diameter, can be used if the density of the core polymer differs sufficiently strongly from the density of the carrier medium or of the continuous phase.

The polymerization of the shell onto the latex core can follow directly after the polymerization of the core material. The method of procedure resembles in principle that described earlier above for the seed latex. The monomer mixture of the shell composition, in which suitably monomers of the Z'RX-type are present, is added per se or as an emulsion in water or a buffer solution over a period of time from 0.5 to 4 hours to the core latex. In this, attention must again be paid that the total emulsifier concentration remains so low that the formation of new particles is avoided. In certain cases, it can be necessary to add two different monomer feeds simultaneously, one of which may possibly contain water. Such a procedure is always necessary if the monomers do not dissolve in one another, or if a part of the monomers is only soluble in water but the other part is not water soluble.

Following these prescriptions, the shell monomer polymerizes on the polymer core which is present. It may prove suitable additionally to add initiator or buffer solution before the addition of the shell monomers, particularly if the polymerization of the latex core does not occur in a buffer solution and if the shell monomers are added in a monomer-addition technique.

The addition of a buffer is above all of extraordinary importance if the functional monomers, $Z'—(R)_n—X$, are highly reactive compounds. Then, the buffer mixture is naturally so adjusted that any disturbance of these reactive groups (e.g. by hydrolysis) is kept as minimal as possible during the course of synthesis of the latex particles.

The polymerization conditions are, with the exception of a limited emulsifier concentration, similar to those which have been described for the preparation of the core. A single batch or multiple batch method is possible; however, a monomer-feed or emulsion-feed method is preferred. The polymerization can occur thermally in the region of about 50° C.–100° C. or it can take place also at lower temperatures with the aid of a redox initiator system. As polymerization initiators, preferably those water-soluble starters which are conventionally used in emulsion polymerization are preferred. In principle, however, oil soluble initiators can also be used providing their decomposition temperature lies in the aforementioned temperature range.

An appropriate ratio of the shell thickness to the size of the core is attained, for example, if the weight of the core material to that of the shell material is in a ratio from 1:3 to 5:1. However, also more extreme core-shell ratios are possible in principle, for example 10:1. It is understood that the shell portion should be chosen to be larger the smaller the latex core is.

The particles are obtained in the form of aqueous dispersions (latices) of a relatively low viscosity. The polymer content can—as a guideline—be in the region from 15–30 percent by weight, for example, in such a dispersion. In principle, however, a solids content from a few percent by weight up to about 70 percent by weight is possible.

When dispersed, the polymer particles generally have a size between about 0,05 micron and about 5 micron, and more often between about 0,5 micron and about 2 microns.

The particles can be recovered as a powder by a variety of techniques such as spray drying, freeze drying, precipitation, etc. In this powdered condition, the primary particles may aggregate loosely to form "superstructures" of varying sizes, but wherein the individual primary particles retain their original size. On redispersion in a liquid, usually an aqueous medium, these "superstructures" swell and revert to the original primary particles.

The dry polymer particles are preferably stored under anhydrous conditions, protected from any reaction with nucleophilic reagents, and suitably below about 50° C.

Redispersion is simply effected by combining the dry particles with a liquid and stirring. The dispersing phase is usually water or an aqueous medium, suitably a medium such as a buffer solution in which a desired further reaction with a biologically active substance can be effected.

The core-shell latices are used for the preparation of diagnostic reagents as follows.

The novel reagents according to the invention can be prepared by a reaction of a latex of the novel core-shell particles with a biologically active substance or structure. The biologically active substances or structures can be, for example, "immunologically active" materials. As "immunologically active" materials, for example, the components of physiological liquids, cell extracts, and tissue extracts can be mentioned, providing that an immunologic anti-reactant is available or can be prepared.

As representative of immunologically active materials, amino acids, peptides, proteins, enzymes, lipoproteins, glycoproteins, lipoids, nucleic acids, polysaccharides, primary amines, alkaloids, hormones, vitamins, sterols, and steroids can be mentioned.

As immunologically active structures, microorganisms such as gram-positive and gram-negative bacteria, spirochetes, mycoplasmas, mycobacteria, vibrionaceae, actinomyces, protozoa such as intestinal protozoa, amebas, flagellates, spores, intestinal nematodes and tissue nematodes (worms), trematodes (schistosomes, leeches), cestodes, and toxoplasmas can be mentioned. Also, fungi such as sporotrichum, cryptococcus, blastomyces, histoplasma, coccidiodies, and candida, viruses and rickettsia such as canine hepatitis, Shope-papilloma, influenza A and B, chicken pox, herpes simplex, adenoviruses, polyomas, Rous-sarcoma, smallpox, polio virus, measles, canine distemper, leukemia, mumps, Newcastle-disease, sendai, echovirus, hoof-and-mouth disease, psittacosis, rabies, extromelia, and tree viruses. Further, tissue antigens, hormones such as the hypophysis hormone, insulin, glycagon, thyroid hormone, chorionic gondatropin, chorionic growth hormone-prolactin, and human placental lactogen are considered, as are enzymes such as pancreatic chymotrypsinogen, procarboxypeptidase, glucose-oxidase, lactate dehydrogenase, uricase, amino acid-oxidase, urease, asparaginase, and proteases. Further, blood cell antigens, blood group substances and other isoantigens such as blood platelets, leucocytes, plasma proteins, milk proteins, saliva proteins, urine proteins, and antibodies, including autoantibodies, can be mentioned.

The use of the core-shell latices for the immobilization of enzymes is discussed more in detail below.

For reactions of the polymer particles according to the invention with enzymes, the enzyme can simply be incubated in an aqueous medium with an adequate amount of the particles. The aqueous medium should preferably approach physiological conditions, for example a buffer adjusted to be suitable to the type of enzyme employed. The materials are incubated preferably not significantly above room temperature and with moderate stirring. If the epoxy group is used as the functional group, one can work in the pH region between 6 and 9, for example, without limitation. In general, a time period from one to several days, for example three days, is appropriate for the reaction. The non-covalently bound enzyme can be separated by repeated centrifugation (at about 5000 rpm) and redispersion in buffer solution. A determination of the activity can follow patterned on the known enzyme-specific determination methods. A particular advantage of the present invention is that even loaded polymer particles can be redispersed—for example in the form of a freeze dried powder—and may optionally be stored over a long period of time. The limiting factor is in any case the stability of the bound biological material.

The polymer particles according to the present invention can also be used as a carrier for other—for instance industrially useful—enzymes in a suitable form. Acylases, penicillinase, glucose-isomerase, and peroxidases should be mentioned, for example, inter alia.

For various reasons, for example for following immunoagglutination, it can be advantageous—as already mentioned—to provide the particles with a marker, for example a fluorescent dyestuff.

The polymer latices of the present invention are suitable for the immobilization of microorganisms in general, for which the reaction conditions are similar to those for the immobilization of proteins. In contrast to the state of the art, the present method offers a better accessability of the immobilized microorganisms for substrate molecules. The small cytotoxicity characteristic of the present immobilization method should be emphasized.

The comments above are valid also for the immobilization of viruses and of eukariotic cells. The polyfunctional nature of the polymer particles also in general permits their use for the crosslinking of biologically active substances. From this viewpoint, those latex particles of small diameter (500 Angstrom units is a guide value) are of particular significance.

The polymer particles of the invention can also be used to advantage in preparative organic syntheses. In this case it is not necessary to operate in an aqueous medium: rather, also organic reaction media can be employed or co-employed.

For example, protective groups can be introduced in this manner. A particularly interesting aspect lies in the use of the materials according to a peptide synthesis according to Merrifield [cf. Merrifield, Adv. Enzymol. 32, 221–296 (1969)].

A better understanding of the present invention and of its many advantages will be had by referring to the following specific Examples, given by way of illustration.

EXAMPLE 1

Preparation of Latex No. 1

(Exemplary of a coarse-particle latex)

(a) Synthesis of a parent dispersion 1600 g of water are introduced into a polymerization vessel equipped with a reflux condenser, stirrer, and thermometer, and are heated to 80° C. After the addition of a monomer mixture comprising
3 g of isobutyl methacrylate,
3 g of methyl methacrylate, and
0.3 g of ethyleneglycol dimethacrylate.
4 g of ammonium persulfate, dissolved in 36 g of water, are added.

Then, at 80° C., a mixture of
200 g of isobutyl methacrylate,
200 g of methyl methacrylate, and
20 g of ethyleneglycol dimethacrylate
is added thereto within a period of two hours. After the end of the monomer addition, the mixture is maintained for one further hour at 80° C. A coagulate-free, readily filterable, dispersion containing about 20 percent solids and of low viscosity is obtained.

(b) Synthesis of a dispersion containing oxirane groups 350 ml of water are introduced into a polymerization vessel equipped with a reflux condenser, stirrer, and thermometer. 10 ml of a phosphate buffer solution (pH=7, "TITRISOL") and 80 g of the parent dispersion are added thereto. After heating to 80° C. to 0.4 g of the sodium salt of 4,4'-azobis-(4-cyanovalerianic acid) in 4 ml of water is added.

Thereafter is added, at 80° C. over a period of three hours, an emulsion comprising
1000 g of water,
1 g of sodium lauryl sulfate,
1 g of the sodium salt of 4,4'-azobis(cyanovaleric acid),
150 g of methyl methacrylate,
150 g of isobutyl methacrylate, and
15 g of ethylene glycol dimethacrylate.
Subsequently, over a period of 60 minutes, the following are added simultaneously: a solution of 20 g of methacrylamide and 0.6 g of the sodium salt of 4,4'-azobis-(4-cyanovalerianic acid) in 300 g of water, as well as a monomer mixture comprising 35 g of methyl methacrylate, 40 g of glycidyl methacrylate, and 4 g of ethylene glycol dimethacrylate. Thereafter, the mixture is stirred for a further 60 minutes at 80° C.

A dispersion free of coagulate and of low viscosity having a solids content of about 20° C. is obtained. The particle size is about 2 microns.

EXAMPLE 2

Preparation of Latex No. 2

(Exemplary of a coarse-particle latex)

(a) Synthesis of a parent dispersion 1600 g of water are introduced into a polymerization vessel like that of Example 1 and warmed to 80° C. After the addition of a monomer mixture comprising
6.24 g of styrene and
0.06 g of allyl methacrylate,
4 g of ammonium persulfate, dissolved in 36 g of water, are added. To this mixture, again at 80° C., a mixture of
415 g of styrene and
5 g of allyl methacrylate
is added dropwise over a period of 2 hours.

After the end of the monomer addition, the mixture is kept for a further 2 hours at 80° C. A viscous dispersion containing about 20 percent solids which is free of coagulates and can be coarsely filtered is obtained.

(b) Synthesis of a dispersion containing oxirane groups

The procedure of Example 1 is followed, but heating is at 85° C. and 1.0 g of the sodium salt of 4,4'-azobis-(4-cyanovaleric acid) in 10 ml of water is added.

To this mixture, an emulsion is added, over a period of 3 hours at 85° C., consisting of:
1000 g of water,
1 g of sodium lauryl sulfate, 4 g of the sodium salt of 4,4'-azobis(cyanovalerianic acid),
312 g of styrene, and
4 g of allyl methacrylate.

Subsequently, over a period of 90 minutes, the following are added simultaneously: a solution of 20 g of methacrylamide and 0.6 g of the sodium salt of 4,4'-azobis-(4-cyanovalerianic acid) in 300 g of water, as well as a monomer mixture comprising 35 g of methyl methacrylate, 40 g of glycidyl methacrylate, and 4 g of ethylene glycol dimethacrylate. The mixture is then stirred for a further 60 minutes at 80° C.

A readily filterable dispersion of low viscosity, free of coagulate and having a solids content of about 20 percent, is obtained. The particle size is about 2 microns.

EXAMPLE 3

Preparation of Latex No. 3

(Exemplary of a fine-particle latex)

5 ml of a phosphate buffer solution (pH=7, "TITRISOL"), 0.03 g of sodium lauryl sulfate, and 0.2 g of the sodium salt of 4,4'-azobis-(4-cyanovalerianic acid) are dissolved in 100 ml of water present in a polymerization vessel equipped as described earlier. The mixture is heated to 80° C. and, over a period of three hours, an emulsion is added comprising
0.1 g of sodium lauryl sulfate,
0.5 g of the sodium salt of 4,4'-azobis(4-cyanovalerianic acid),
80 g of methyl methacrylate,
15 g of [2-(2,4,6-tribromophenoxy)ethyl]-methacrylate,
5 g of ethylene glycol dimethacrylate, and
200 g of water.

Subsequently, a solution of 5 g of methacrylamide in 75 g of water and a monomer mixture comprising
10 g of glycidyl methacrylate,
1 g of ethylenglycol dimethacrylate, and
9 g of methyl methacrylate
are added simultaneously over a period of 90 minutes. The mixture is held for a further 60 minutes at 80° C.

A dispersion of low viscosity having a solids content of about 25 percent is obtained. The particle size is 0.3 micron. The content of oxirane groups is 31 percent, based on the glycidyl methacrylate introduced (determined by titration with sodium thiosulfate).

EXAMPLE 4

Preparation of Latex No. 4

(a) Preparation of a core dispersion
0.3 g of sodium tetradecyl sulfonate,
0.6 g of ammonium sulfate, and
500 g of distilled water
are introduced into a polymerization vessel equipped as in Example 1 and are warmed to 80° C.

An emulsion comprising
500 g of p-bromostyrene,
300 g of fumaric acid diethyl ester,
4 g of sodium tetradecyl sulfonate,
4 g of sodium persulfate, and
710 g of distilled water
is introduced into this mixture dropwise at 80° C. over a period of 6 hours.

After the introduction, the mixture is stirred for a further two hours at 80° C., then cooled to room temperature and filtered. The dispersion obtained is of low viscosity and has a solids content of about 40 percent.

(b) Preparation of a core-shell dispersion 500 g of the 40 percent dispersion of Example 4(a) are adjusted with phosphate buffer to a pH of 7.0 and are diluted to a total volume of 1000 ml with a solution comprising 1 g of the sodium salt of 4,4'-azobis-(cyanovalerianic acid) and 0.5 g of sodium tetradecyl sulfonate in 1000 ml of distilled water. [This is equivalent to a 20 percent dispersion as in Example 4(a) at a pH of 7.0].

This mixture is heated to 80° C. in a polymerization vessel, held for 15 minutes at this temperature, and then the following two solutions are introduced dropwise at 80° C., simultaneously:

Solution A:
20 g of 2-bromoethyl methacrylate,
2.5 g of glycol dimethacrylate,
17.5 g of N-t.-butyl methacrylamide, and
10 g of methyl methacrylate;

Solution B:
1 g of the sodium salt of 4,4'-azobis-(cyanovalerianic acid) in
50 g of distilled water.

The total time for dropwise addition is about two hours. For both additions, the rate of addition should be as closely the same as possible. After the end of the addition, the mixture is kept for one further hour at 80° C. Thereafter, it is cooled and filtered. A dispersion of low viscosity containing fine particles and having a solids content of about 23 percent is obtained.

(c) Preparation of the core-shell dispersion

Example 4(b) is followed (dilution of dispersion 4(a) neutralization, etc.) but the following solutions are added.

Solution A:
10 g of vinyl acetate,
30 g of chloroacetic acid vinyl ester,
2.5 g of methylene-bis (acrylamide), and
7.5 g of acrylamide.

Solution B:
2 g of the sodium salt of 4,4'-azobis-(cyanovaleric acid) in 50 g of distilled water.

The total time of dropwise addition is about 3 hours. After addition is concluded, the mixture is kept for a further 2 hours at 80° C. After cooling and filtration, a low viscosity dispersion containing fine particles is obtained.

EXAMPLE 5

Synthesis of Latex No. 5

Stage I

The following components are introduced into a polymerization vessel as in Example 1:
1550 g of distilled water,
0.8 g of sodium lauryl sulfate,
3.2 g of methyl methacrylate, and
3.2 g of isobutyl methacrylate
and are then warmed to 80° C. with stirring. Subsequently, a solution of 4 g of ammonium persulfate in 40 ml of water is added. Thereafter, the following monomer mixture is added at 80° C.:
190 g of methyl methacrylate,
190 g of isobutyl methacrylate, and
20 g of glycol-bis(methacrylate).

The time for addition of the monomer is two hours. After addition, the mixture is kept for a further two hours at 50° C. After cooling, a readily filterable dispersion free of coagulate is obtained having a solids content of 19 percent, a pH of 2.2, and viscosity of 4 mPa.sec.

Stage II 160 g of the dispersion of stage I are introduced into a polymerization vessel as in Example I and the following are added:
10 g of phosphate buffer (pH=7, "TITRISOL"),
0.4 g of the sodium salt of 4,4'-azobis-(cyanovalerianic acid), and
310 g of distilled water.
This mixture is warmed to 80° C. and the following emulsion is added over a period of 3 hours:
143 g of methyl methacrylate,
143 g of isobutyl methacrylate,
15 g of ethylene glycol-bis(methacrylate),
1 g of sodium lauryl sulfate,
1.8 g of sodium salt of 4,4'-azobis(cyanovalerianic acid), and
970 g of distilled water.
Immediately thereafter, the following two mixtures are added simultaneously over a period of one hour:
Mixture A:
44 g of methyl methacrylate,
4 g of ethylene glycol-bis(methacrylate), and
42 g of glycidyl methacrylate;
Mixture B:
0.6 g of the sodium salt of 4,4'-azobis-(cyanovalerianic acid),
10 g of methacrylamide, and
320 g of distilled water.
After the addition, the mixture is kept for a further hour at 80° C. After cooling, a coagulate-free dispersion having a solids content of about 19 percent is obtained. The particle size is about 0.4 micron.

EXAMPLE 6

Purification of the latex according to Example 1

(Removal of the auxiliaries, emulsifiers, initiators, etc. required for the synthesis)

10 ml of the dispersion of Example 1 are centrifuged for 15 minutes at 5000 rpm. The remaining serum is poured off and the particles are subsequently redispersed in 1N NaCl (equivalent to 1 g of polymer solids in about 50 ml of 1N NaCl). These are then again centrifuged for 10 minutes at 5000 rpm and decanted. Redispersion in 1N NaCl and centrifugation are repeated two more times.

The particles are then redispersed in 0.05M phosphate buffer at pH 7.5 (equivalent to 1 g of polymer solids in 50 ml of 0.05M phosphate buffer at pH 7.5). This is then centrifuged for 10 minutes at 5000 rpm and the residue is poured off.

This procedure is repeated once more. The latex so obtained is then stored in a refrigerator at +5° C.

EXAMPLE 7

Purification of the latex according to Example 3

The procedure of Example 6 is followed, but the duration of centrifugation (5000 rpm) is raised to 30 minutes in each case.

EXAMPLE 8

Reaction for the immobilization of Trypsin 15 ml of the dispersion of Example 1 (containing about 3 g of solid polymer) are combined with 300 mg of trypsin (dissolved in 6 ml of 1M phosphate buffer at pH 7.5). The mixture is then stirred at 23° C. for 72 hours.

Non-covalently bonded enzyme is then removed by a three-fold centrifugation and redispersion in 0.05M phosphate buffer (procedure as in Example 6).

EXAMPLE 9

Measurement of the activity of the immobilized enzyme (a) Hydrolysis of N-benzoyl-arginine-ethyl ester (BAEE) at 37° C. and at an automatically maintained constant pH of 7.5;

1 g of the dry substance of the latex purified by centrifugation according to Example 8 (and introduced as about 2 g of moist substance with about 1 g of water) is dispersed in 20 ml of a 2 percent BAEE-solution.

| Cycle | Activity (U/g) |
| --- | --- |
| 1. | 14.2 |
| 2. | 12.1 |
| 3. | 11.8 |
| 4. | 11.8 |

The activity is in each case referred to 1 g of carrier material. 1 U corresponds to 1 micromol/minute based on the initial rate of reaction. For each sample, 3 to 4 subsequent determinations (cycles) are carried out to discriminate between bound and unbound trypsin.

(b) Hydrolysis of casein (37° C., pH 8.0)

1 g of the dry latex purified by centrifugation according to Example 8 (introduced as about 2 g of moist substance with about 1 g of water) is dispersed in 20 ml of a 4 percent casein solution.

| Cycle | Activity (U/g) |
| --- | --- |
| 1. | 3.2 |

EXAMPLE 10

Freeze drying of a reactive latex 15 ml of the dispersion of Example 1 are purified as in Example 6. A polymer containing about 50 percent of residual moisture is obtained.

This centrifuged latex is freeze dried and is subsequently stored for 6 months at −20° C.

Redispersion of the freeze dried latex:

Redispersion follows in 0.05M phosphate buffer at pH 7.5. The mixture must be vigorously stirred for about 5 minutes. Alternatively, the sample suspended in the buffer solution can be treated briefly with ultrasound.

Subsequently, the material is reacted with an enzyme as in Example 8 (10 percent of trypsin, calculated on the latex introduced).

The activity of the freeze dried latex, stored for six months at −20° C., redispersed, and reacted with 10 percent of trypsin is reported below:

| Cycle | Activity (U/g) (Substrate: BAEE) | Activity (U/g) (Substrate: Casein) |
| --- | --- | --- |
| 1. | 13.3 | 2.9 |
| 2. | 10.6 | 2.2 |
| 3. | 10.6 | 2.2 |

EXAMPLE 11

Freeze drying of a latex having trypsin immobilized thereon 1 g of the latex of Example 8, reacted with trypsin, if freeze dried and stored thereafter for 6 months at −20° C. Redispersion follows as described in Example 10, with 0.05M phosphate buffer.

The activity toward casein (1 g of redispersed latex solids in 20 ml of 4 percent casein solution) at 37° C. and pH 8.0 is reported below:

| Cycle | Activity (U/g) |
| --- | --- |
| 1. | 3.6 |
| 2. | 2.4 |
| 3. | 2.4 |

EXAMPLE 12

The immobilization of trypsin

The procedure of Example 8 is followed but 15 ml of the dispersion of Example 3 (centrifugation for 30 minutes at 5000 rpm) are used for the immobilization of trypsin.

The activity toward casein as a substrate (pH 8.0, 37° C.) is reported below:

| Cycle | Activity (U/g) |
| --- | --- |
| 1. | 5.5 |
| 2. | 4.2 |
| 3. | 4.0 |

EXAMPLE 13

Synthesis of a fluorescently marked latex 40 g of the parent dispersion of Example 1(a) are introduced into a polymerization vessel according to Example 1. 5 ml of phosphate buffer (pH=7, "TI-TRISOL"), 0.2 g of the sodium salt of 4,4'-azobis-(cyanovalerianic acid), and 180 g of distilled water are added thereto.

After warming of the mixture to 80° C., an emulsion is added over a period of 3 hours—also at 80° C.—comprising the following:
127 g of methyl methacrylate,
15 g of isobutyl methacrylate,
7.5 g of ethylene glycol-bis(dimethacrylate),
0.6 g of flurol-green-gold [=solvent green 5 (Colour Index Part I, No. 79075)],
1.0 g of the sodium salt of 4,4'-azobis-(cyanovalerianic acid),
0.5 g of sodium lauryl sulfate, and
450 g of distilled water.
After conclusion of the addition (=latex core), the following two mixtures are added at 80° C. simultaneously over a period of one hour:
Mixture A:
24 g of methyl methacrylate,
2 g of ethylene glycol-bis(methacrylate), and
21 g of glycidyl methacrylate;
Mixture B:
3 g of methacrylamide,
0.3 g of the sodium salt of 4,4'-azobis-(cyanovalerianic acid), and
155 g of distilled water.

After conclusion of the addition, the mixture is held for a further 60 minutes at 80° C. and is then cooled.

A readily filterable dispersion, free of coagulate and having a solids content of 19 percent, a pH of 7.7, and a viscosity of 10 mPa.sec. is obtained. Particle size is about 2 microns.

The fluorescence under UV stimulation is clearly visible macroscopically as well as in a fluorescence microscope.

EXAMPLE 14

Immobilization of anti-albumin 10 ml of the dispersion according to Example 5 are diluted to 100 ml with 0.05M of phosphate buffer at pH 7.5. (Suitably, 0.05 percent of sodium azide is added to the phosphate buffer.) A dispersion contained about 2 percent of polymer solids results.

The anti-serum identified as Cat. No. 61-015,6389 (goat) in the catalog of Miles-Yeda, Ltd., (Kiryat Weizmann, Rehoboth, Israel) is diluted with buffer to the following concentrations:
(a) 1000 micrograms of antibody/ml
(b) 200 micrograms of antibody/ml
(c) 40 micrograms of antibody/ml
(d) 8 micrograms of antibody/ml
(e) 0 micrograms of antibody/ml The bonding of the anti-albumin onto the latex particles occurs by reaction, in each case, of 1 ml of the 2 percent dispersion with 1 ml of the dilution series (a)–(e). The mixtures are stirred for 5 days at room temperature and the latex particles are purified by centrifugation as described in Example 6.

The product can be used directly for the detection of human albumin using the latex agglutination technique.

EXAMPLE 15

Synthesis of a compound containing deuterium as a marker

In 2 ml of purified methylene chloride as a solvent, 0.146 g (1 m mols) of deuterated benzoyl chloride-$d_5$ is reacted with 0.18 g (3 m mols) of ethanol amine during 1 day at 0° C. and 1 day at ambient temperature. Thereafter, the methylene chloride is vaporized and the residue is mixed with an amount of the polymeric material of Example 10 containing 5 m mol equivalents of oxirane groups and the mixture is adjusted to pH 8 by the addition of aqueous phosphate buffer solution. After 3 days at 37° C., the mixture is diluted with distilled water and the latex containing the excess of ethanol amine in covalently bound form is centrifuged. The supernatant aqueous solution contains the desired end product, N-2-hydroxyethyl benzoyl amide-$d_5$, which is ready for use in biological test.

What is claimed is:

1. A polymer particle, redispersible in a liquid to form a dispersion and having a protein, virus, or microorganism covalently bound thereto, said particle having an average particle diameter between about 0.05 micron and about 5 microns and having an inner core of a polymer imparting dispersibility and stability of form to said particle and an outer shell of a different polymer over said core, the ratio by weight of the polymer of the core to the weight of the polymer of the shell being between 1:3 and 10:1, the polymer of said core being an intrinsically hard polymer having a $T\lambda_{max}$ of at least 0° C. or being an intrinsically soft polymer having a $T\lambda_{max}$ less than 0° C. which is internally crosslinked, the different polymer of said shell being hydophilic and being internally crosslinked, crosslinked or grafted to said core, or both internally crosslinked and crosslinked or grafted to said core, and having a $T\lambda_{max}$ of 20° C.–250° C. in an anhydrous condition, said shell polymer, prior to bonding with said protein, virus, or microorganism having functional groups reactive with nucleophilic groups of said protein, virus, or microorganism to bond said protein, virus, or microorganism covalently to said particle, and being bonded to said protein, virus, or microorganism by the reaction of said functional groups with nucleophilic groups of said protein, virus, or microorganism.

2. A redispersible polymer particle as in claim 1 wherein the polymer of said shell is free of monomers having an aromatic group therein.

3. A redispersible polymer particle as in claim 1 wherein the polymer of said shell is electrically neutral.

4. A redispersible polymer particle as in claim 1 wherein the polymer of said core is intrinsically soft, but is crosslinked.

5. A redispersible polymer particle as in claim 1 wherein the polymer of said core is intrinsically hard.

6. A redispersible polymer particle as in claim 1 wherein the polymer of said shell comprises (a) from 4.9 to 99.9 percent, by total weight of the polymer material of said shell, of a combination of (1) at least one vinyl monomer which prior to bonding has a functional group reactive with nucleophilic groups of said protein, virus, or microorganism to bond said protein, virus, or microorganism to said particle, and (2) at least one vinyl monomer containing a hydrophilic group, the content of said monomer having a functional group being at least 0.1 percent;

(b) from 0 to 95 percent by weight of at least one vinyl monomer free of hydrophilic groups; and (c) from 0.1 to 20 percent by weight of at least one crosslinking monomer which is an ester of a polyalcohol and at least one member selected from the group consisting of acrylic acid and methacrylic acid, said ester having a plurality of acrylate, methacrylate, or acrylate and methacrylate groups.

7. A redispersible polymer particle as in claim 6 wherein said monomer having a functional group reactive with nucleophilic groups of a protein, virus, or microorganism to bond the protein, virus, or microorganism to the particle is of the formula $$Z'-(R)_n-X$$

wherein Z' is a group including a polymerizable vinylic unsaturation, R is a spacing unit, n is 0 or 1, and X is a functional group reactive with nucleophilic groups of a protein, virus, or microorganism in aqueous solution in the pH region from 6.0 to 9.0.

8. A polymer particle as in claim 1 having a protein bound thereto, which protein is an antigen or an antibody.

9. A polymer particle as in claim 8 having an antibody bound thereto.

10. A polymer particle as in claim 1 having a microorganism bound thereto.

11. A polymer particle as in claim 1 having a virus bound thereto.

12. A polymer particle as in claim 1 having a protein bound thereto, which protein is an enzyme.

* * * * *